United States Patent [19]

Sloan

[11] Patent Number: 5,409,004
[45] Date of Patent: Apr. 25, 1995

[54] LOCALIZATION DEVICE WITH RADIOPAQUE MARKINGS

[75] Inventor: Dale A. Sloan, Fort Wayne, Ind.

[73] Assignee: Cook Incorporated, Bloomington, Ind.

[21] Appl. No.: 224,115

[22] Filed: Apr. 6, 1994

Related U.S. Application Data

[63] Continuation of Ser. No. 75,767, Jun. 11, 1993, abandoned.

[51] Int. Cl.6 .............................................. A61B 5/00
[52] U.S. Cl. ..................................... 128/657; 604/164; 604/117
[58] Field of Search ............ 128/653.4, 654, 656–658, 128/653.1; 604/116–117, 164–169, 280–281, 130

[56] References Cited

U.S. PATENT DOCUMENTS

| | | |
|---|---|---|
| 2,922,420 | 1/1960 | Cheng . |
| 4,058,114 | 11/1977 | Soldner . |
| 4,582,061 | 4/1986 | Fry ................................. 128/654 X |
| 4,691,333 | 9/1987 | Gabriele . |
| 4,727,565 | 2/1988 | Ericson . |
| 4,841,967 | 6/1989 | Chang et al. . |
| 4,875,478 | 10/1989 | Chen . |
| 5,056,523 | 10/1991 | Hotchkiss . |
| 5,059,197 | 10/1991 | Urie et al. ........................ 128/658 X |
| 5,078,142 | 7/1992 | Siczek et al. ..................... 128/653.1 |
| 5,142,557 | 8/1992 | Toker et al. . |
| 5,158,084 | 10/1992 | Ghiatas ................................ 128/657 |
| 5,253,653 | 10/1993 | Daigle et al. .................... 604/280 X |

*Primary Examiner*—Angela D. Sykes
*Attorney, Agent, or Firm*—Richard J. Godlewski

[57] ABSTRACT

The present invention involves the localization of lesion tissue within the breast. A surgical guidewire or needle includes a plurality of visual and radiopaque markers along its axial length so that the position of the lesion tissue may be determined in relation to the markers. In one form, the markers are portions extending from the guidewire or needle. In a second form, the markers are grooves formed in the guidewire or needle. The markers are disposed at predetermined distances of about one centimeter, and are differentiable so that the needle or guidewire serves as a metered marker perceptible in a mammogram or visually during surgery.

20 Claims, 3 Drawing Sheets

LOCALIZATION DEVICE WITH RADIOPAQUE MARKINGS

This is a continuation of application Ser. No. 08/075,767 filed on Jun. 11, 1993, now abandoned.

BACKGROUND OF THE INVENTION

1. Field of the Invention

The present invention relates to medical devices used in needle localization procedures for locating lesions within the body. More specifically, the field of the invention is that of devices used to localize small nonpalpable lesions.

2. Description of the Related Art

To detect small nonpalpable lesions within the breast, women have mammographies performed periodically. Mammography involves the radiographic examination of the breast for nonpalpable lesions, so that the lesions, which are normally undetectable by sight or feel, may be visually identified on the radiogram or x-ray. The lesion areas may include cancerous or other diseased tissue which should be removed. Early detection and removal of cancerous lesions can greatly improve a patient's ability to avoid life or limb threatening complications. Although many lesions are ultimately determined to be benign, it is generally recommended that a woman have frequent mammographies as a precaution against cancerous growths.

In current practice, if a lesion is detected in the breast, a guidewire, needle, or similar device is placed in the breast tissue as close as possible to the lesion so that it may be identified and located during surgery. The tissue which has the lesion is located in relation to the position of the needle within the body tissue. First, the lesion must be detected by mammography. Second, assuming a lesion is detected, a second mammogram is taken with the needle positioned in the breast tissue. If the needle is sufficiently close to the lesion in both the craniocaudal and mediolateral mammograms, then the patient is prepared for surgery. If the needle is not positioned correctly, this procedure is repeated until the lesion is appropriately positioned to locate the lesion.

Although the needle itself could be used for location of the lesion, generally the needle includes a hollow axial center for the introduction of marking material to identify the tissue. Two different methods are used to identify the tissue, which can be used separately or jointly. The first method uses a guidewire which is introduced through the needle and anchored into the breast tissue. The second method uses a tissue staining dye which is injected by the needle into the tissue around the lesion. Later in the day, surgery is performed wherein a cylinder of tissue around the position of the needle is removed. The cylinder of tissue to be removed is determined by the position of the needle, guidewire, or dyed tissue within the breast. However, because of the possibility that body tissue has shifted between the taking of the mammogram and the surgical procedure, the size and extent of the cylinder of tissue being removed is relatively large to minimize the chance of missing a significant portion of the lesion tissue.

A difficulty in the prior art procedures involves the depth of the lesion tissue in the breast. The location of tissue within the breast is altered when positioned within the mammography machine so that by the time of surgery, the lesion tissue frequently has moved to a different position. Also, it is difficult to determine the exact location of the lesion along the axial length of the needle from the two views of the mammogram.

To compensate for the shifting and movement of tissue and the inexact determination of the location of the lesion, a relatively large cylindrically shaped portion of tissue is removed during surgery to ensure that the entire lesion is removed. However, this cylindrically shaped portion of tissue is often much more tissue than is necessary which results in the undesirable removal of healthy tissue. Occasionally, the lesion tissue is not completely removed because of the inaccuracies in determining location of the lesion tissue. Further, for some patients who may have several lesions requiring removal, a substantial amount of healthy tissue may be undesirably removed.

What is needed is a device and procedure for the identification of lesion tissue within the breast which allows the accurate removal of the lesion tissue and a minimal amount of healthy tissue.

SUMMARY OF THE INVENTION

The present invention relates to an improved needle localization device which includes radiopaque distance markings along the axial length of the guidewire or needle so that the location and depth of the lesion may be determined from the mammogram. By use of the present invention, the surgeon may determine the depth of the lesion tissue by examination of the position of the lesion tissue with respect to the marked axis of the guidewire or needle. The ability of the surgeon to remove the lesion tissue accurately while minimizing the amount of healthy tissue removed is greatly enhanced by the present invention.

The device of the present invention is similar to prior art guidewires or needles. However, at predetermined positions along the axial length of the guidewire or needle, the present invention includes visual and radiopaque markings so that the axial position may be determined radiographically from a mammogram, or visually during surgery. In this manner, the angular position of the two mammograms relative to the guidewire or needle is of lesser consequence, because the radiographic markings disclose the axial position of the lesion relative to the axis of the guidewire or needle.

In one form of the present invention, a series of spaced apart unit length marking portions are periodically disposed along the axial length of the guidewire or needle. The size and number of markings is different for each predetermined position, so that the guidewire or needle acts as a ruler by which the position of the lesion tissue can be more accurately measured. In another form of the present invention, a series of spaced apart grooves are formed on the guidewire or needle, forming unit length marking gaps along the axial length. In either embodiment, barbed or hooked ends are used to locate the end of the guidewire or needle in the breast tissue, so that the guidewire or needle stays in the tissue.

An advantage of the present invention is that more accurate determinations of the location of lesion tissue may be made using the radiopaque markings on the guidewire or needle. By more accurately locating lesion tissue, the chance of not removing lesion tissue is minimized while minimizing the amount of healthy tissue removed. Further, the present invention is compatible with current mammography and surgical techniques, so that the present invention may easily be incorporated into existing procedures and equipment.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1:
FIG. 1 is a side view of a prior art guidewire.

Corresponding reference characters indicate corresponding parts throughout the several views. The exemplification set out herein illustrates preferred embodiments of the invention, in several forms, and such exemplifications are not to be construed as limiting the scope of the invention in any manner.

DESCRIPTION OF THE PREFERRED EMBODIMENTS

The preferred embodiments disclosed below are not intended to be exhaustive or limit the invention to the precise forms disclosed in the following detailed description. Rather, the embodiments are chosen and described so that others skilled in the art may utilize their teachings.

Figure 2:
FIG. 2 is a side view of another prior art guidewire.
Figure 3:
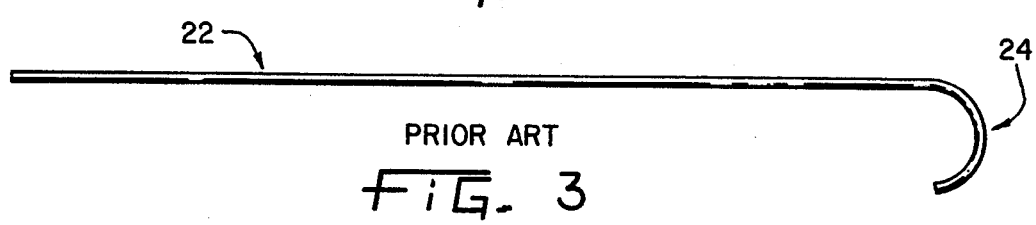
FIG. 3 is a side view of a third prior art guidewire.

The present invention is perhaps best understood when compared to devices and procedures already known in the prior art. FIGS. 1-5 illustrate several prior art devices and the procedure used to identify lesions in the breast. FIGS. 1-3 depict three versions of a localizing guidewire, or similar elongated medical instrument intended for percutaneous insertion into a body cavity. As used in this application, the term guidewire encompasses guidewires, needles (with or without axial bores), or similar devices which are implanted in the breast tissue to determine the position of the lesion. Also, while this invention is particularly described as it relates to lesions in breast tissue, the invention may be applied in similar medical procedures involving radiographic determination of lesion tissue location.

Guidewire 12 of FIG. 1 is a barbed-type guidewire having an acutely angled barb 14 located at its end. Barb 14 is structured and arranged to embed itself within body tissue so that guidewire 12 does not move significantly between the time the mammogram is taken and the time of surgery.

Guidewire 16 of FIG. 2 is a barbed-type guidewire like that of FIG. 1, and includes acutely angled barb 18 at its end. Barb 14 is structured and arranged to embed itself within body tissue so that guidewire 16 does not move significantly between the time the mammogram is taken and the time of surgery. Guidewire 16 further includes thickened portion 20 which acts to further anchor guidewire 16 within the body tissue.

Figure 4:
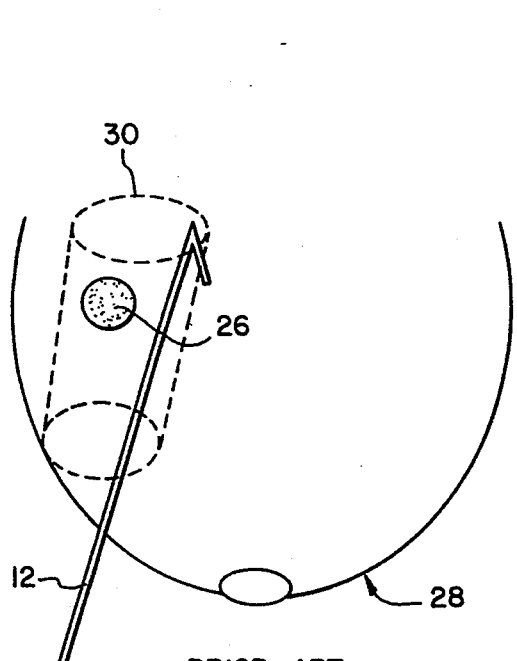
FIG. 4 is a craniocaudal sectional view of a prior art guidewire located within a breast.
Figure 5:
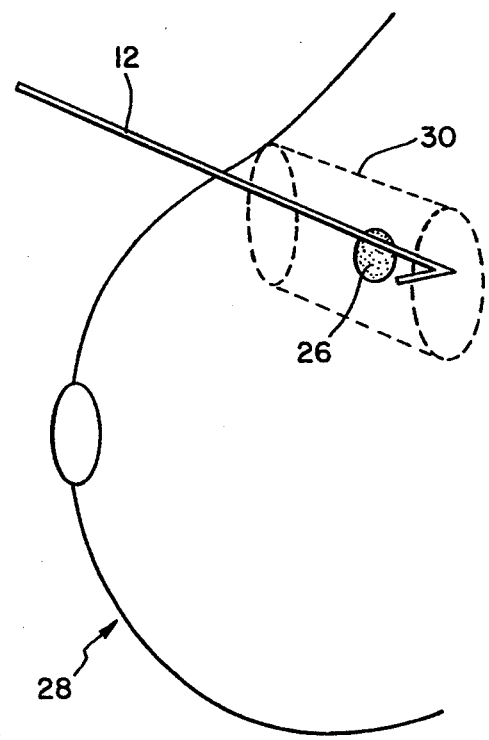
FIG. 5 is a mediolateral sectional view of a prior art guidewire located within a breast.

Guidewire 22 of FIG. 3 is a hook-type guidewire having a half-ring shaped hook 24 at its end. Hook 24 is structured and arranged to embed itself within body tissue so that guidewire 22 does not move significantly between the time the mammogram is taken and the time of surgery, FIGS. 4 and 5 illustrate the procedure used to identify and mark the location of lesion tissue using guidewire 12. Once lesion tissue 26 is discovered in a mammogram of breast 28, guidewire 12 is inserted into the tissue and a mammogram is taken with guidewire 12 located in breast 28. If guidewire 12 is sufficiently close to lesion tissue 26, then the patient may be prepared for surgery by securing guidewire 12 within breast 28, for example by embedding guidewire 12 through a hollow needle. However, if guidewire 12 is not sufficiently close to lesion tissue 26, then the process is repeated until the position of guidewire 12 relative to lesion tissue 26 is sufficiently close to use as a marker during surgery.

Figure 12:
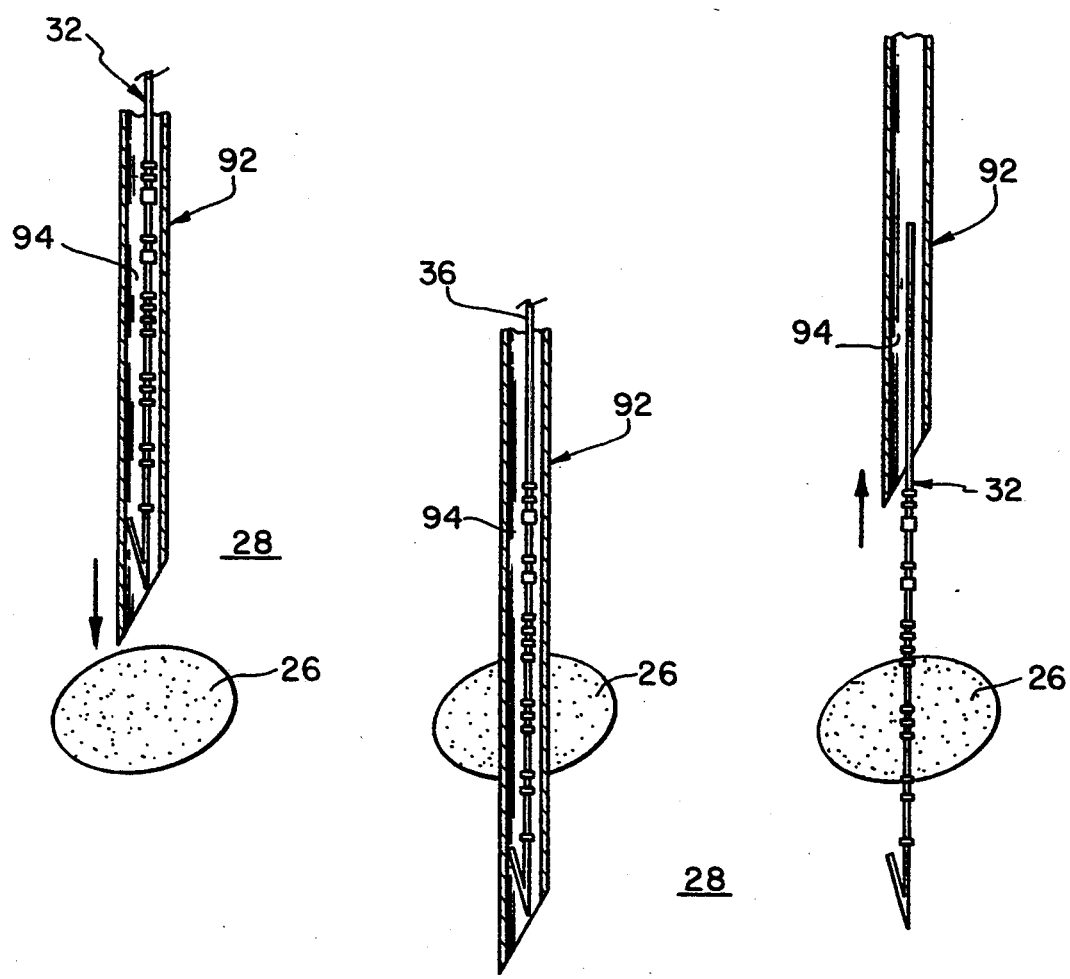
FIG. 12 is a side view, in partial cross-section, of a guidewire of the present invention being implanted within body tissue.

During surgery, the guidewire is used to identify the tissue to be removed. As mentioned above, in order to ensure complete removal of lesion tissue 26 given the inexact determination of the location of lesion tissue 26, a relatively large portion of tissue is removed. The amount of tissue removed is shown on FIGS. 4 and 5 as cylindrical tissue region 30, which is elongated because of the difficulty of determining the position of lesion tissue 26 in relation to the axial length of guidewire 12 and the movement of tissue between the time of the mammography and the time of surgery, while the diameter of the cylinder can be maintained within known error margins because the distance between the lesion and the guidewire is subject to less movement, Several embodiments of the present invention are shown in FIGS. 6-9, while their use is illustrated in FIGS. 10-12. Each guidewire includes an anchor portion at one end which is structured and arranged to embed the guidewire within the breast tissue so that the guidewire does not move significantly between the time the mammogram is taken and the time of surgery. Guidewires 32 and 34 of FIGS. 6 and 8, respectively, are barb-type guidewires having acutely disposed barbs 36 and 38, respectively, located at their ends. Guidewires 40 and 42 of FIGS. 7 and 9, respectively, are hook-type guidewires having half-ring shaped hooks 44 and 46, respectively, located at their ends.

Figure 6:
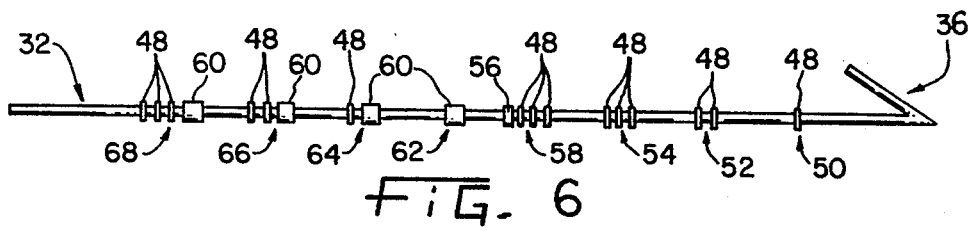
FIG. 6 is a side view of a first embodiment of the present invention.
Figure 7:
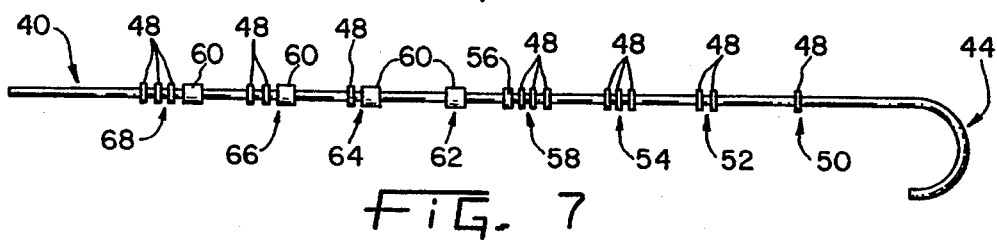
FIG. 7 is a side view of a second embodiment of the present invention.

In accordance with the present invention, each guidewire includes a series of visual and radiopaque markings located at predetermined distances along the axial length of the guidewire. In the disclosed embodiments, the visual and radiopaque markings measure periodic unit distances from the anchor portion of the guidewire. In FIG. 6, guidewire 32 is shown having a single unit length marker portion 48 at axial location 50, two unit length marker portions 48 at axial location 52, three unit length marker portions 48 at axial location 54, three unit length marker portions 48 and a four unit marker 56 at axial location 58. Unit length marker portions 48 and four unit marker 56 are indicia elements which are structured and arranged to be radiographically and visually perceptible. Further, each series of indicia elements at each axial position starts at a predetermined position, e.g., at periodic one centimeter intervals. The indicia elements continue with one five unit length marker 60 at axial location 62, one five unit length marker portion 60 and unit length marker portion 48 at axial location 64, one five unit length marker portion 60 and two unit length marker portions 48 at axial location 66, and one five unit length marker port, ion 60 and three unit length marker portions 48 at axial location 68. Five unit length marker portion 60 is a radiographically and visually perceptible marker or indicia element which is noticeably larger than single unit marker portions 48. Guidewire 40 has a similar series of indicia elements as does guidewire 32, and the similar indicia elements are similarly numbered in FIG. 7.

Figure 8:
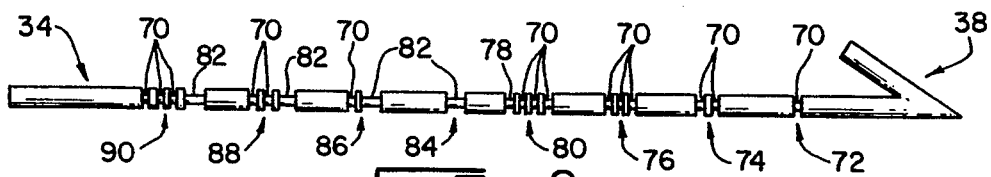
FIG. 8 is a side view of a third embodiment of the present invention.
Figure 9:
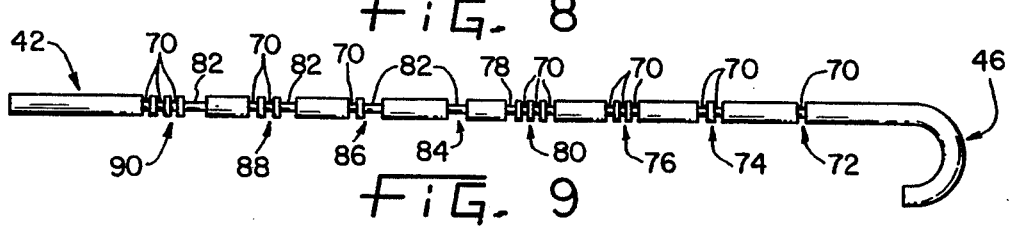
FIG. 9 is a side view of a fourth embodiment of the present invention.
Figures 10, 11:
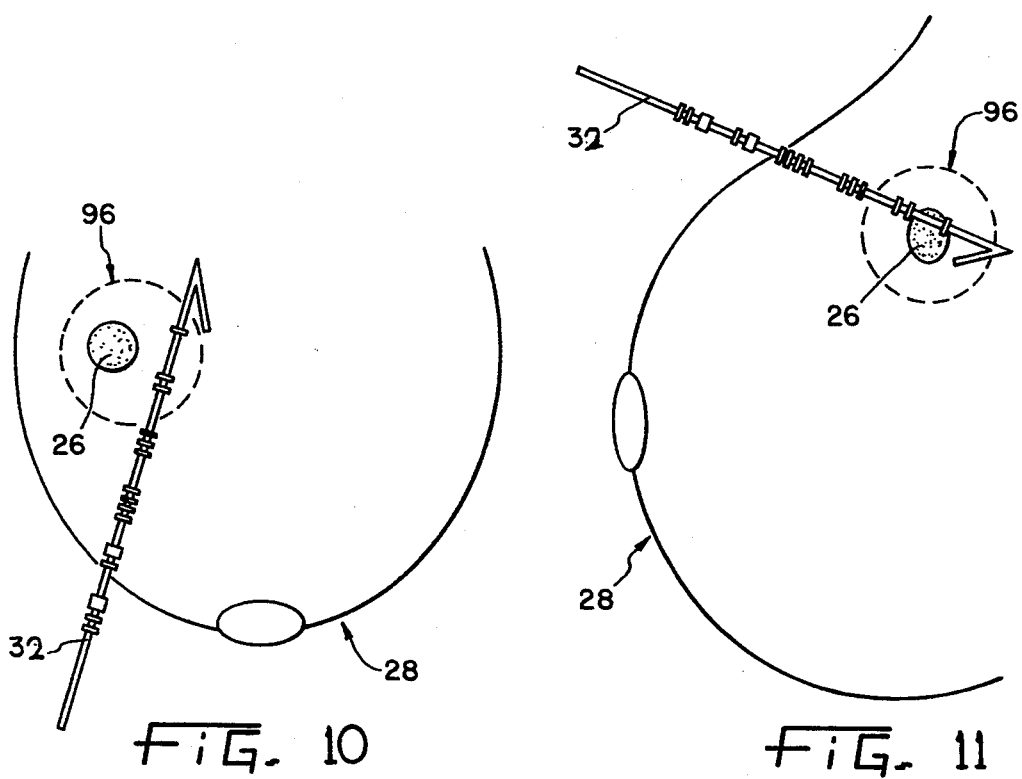
FIG. 10 is a craniocaudal sectional view of a guidewire of the first embodiment located within a breast.
FIG. 11 is a mediolateral sectional view of a guidewire of the first embodiment located within a breast.

Alternatively, FIGS. 8 and 9 show the indicia elements as comprising grooves within guidewires 34 and 42, respectively. In FIG. 8, guidewire 34 is shown having a single unit length marker groove portion 70 at axial location 72, two unit length marker groove portions 70 at axial location 74, three unit length marker groove portions 70 at axial location 76, three unit length marker groove portions 70 and a four unit marker groove 78 at axial location 80. Unit length marker groove portions 70 and four unit marker groove 78 are indicia elements which are structured and arranged to be radiographically and visually perceptible. Further, each series of indicia elements at each axial position starts at a predetermined position, e.g., at periodic one centimeter intervals. The indicia elements continue with one five unit length marker groove portion 82 at axial location 84, one five unit length marker groove portion 82 and unit length marker groove portion 70 at axial location 86, one five unit length marker groove portion 82 and two unit length marker groove portions 70 at axial location 88, and one five unit length marker groove portion 82 and three unit length marker groove portions 70 at axial location 90. Five unit length marker groove portion 82 is a radiographically and visually perceptible marker or indicia element which is noticeably larger than single unit marker groove portions 70. Guidewire 42 has a similar series of indicia elements as does guidewire 34, and the similar indicia elements are similarly numbered in FIG. 9.

FIGS. 10 and 11 illustrate the procedure used to identify and mark the location of lesion tissue using guidewire 32, although any of guidewires 32, 34, 40, and 42 could be employed with similar results. If lesion tissue 26 is discovered in a mammogram of breast 28, guidewire 32 is inserted into breast 28 and a mammogram is taken with guidewire 32 located in breast 28. If guidewire 32 is sufficiently close to lesion tissue 26, then the patient may be prepared for surgery by securing guidewire 32 within breast 28, for example by embedding guidewire 32 through the axial hollow of a needle. However, if guidewire 32 is not sufficiently close to lesion tissue 26, then the process is repeated until the position of guidewire 32 relative to lesion tissue 26 is sufficiently close to use for locating the diseased tissue during surgery.

FIG. 12 depicts the deposit of guidewire 32 into the tissue of breast 28. Hollow needle 92 includes an axial aperture 94 which houses guidewire 32. Once hollow needle 92 is inserted at a depth beyond lesion tissue 26, guidewire 32 may be implanted in breast 28 and hollow needle 92 removed. Thus situated, the surgeon may locate lesion tissue 26 by its position vis-a-vis indicia elements along the axial length of guidewire 32.

During surgery, the guidewire is used to identify the tissue to be removed. The amount of tissue removed is shown on FIGS. 10 and 11 as spherical tissue region 96, which is focused around a particular axial position of guidewire 32 because the location of lesion tissue 26 in relation to the axial position of guidewire 32 may be determined by use of the indicia elements on guidewire 32. The distance of lesion tissue 26 from guidewire 32 may be determined conventionally, which in combination with the determined axial position of lesion tissue 26 defines spherical tissue region 96. The ability of the surgeon to identify spherical tissue region 96 provides the advantages of more accurately removing lesion tissue 26 while minimizing the amount of healthy tissue removed from breast 28.

Although not shown in the Figures, guidewires 32, 34, 40, and 42 may be provided with an external coating of a radiolucent material and thereby provide a sheath over the indicia elements so that a smooth surface is presented along the axial length of the guidewires. The sheath may be used to minimize any irritation to the body tissue, although the resulting guidewires would be thicker and complicate the initial location of the guidewire in the tissue.

While this invention has been described as having a preferred design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An apparatus for determining the location of lesions within tissue, said apparatus comprising:
   an elongated body adapted to be implanted in the tissue; and
   a plurality of indicia means located at predetermined locations on said elongated body, said indicia means being radiopaque, each one of said indicia means being distinctly perceptible and differentiable from any other of said indicia means, whereby the location of lesions radiographically detected may be determined relative to the axis of said body.

2. The apparatus of claim 1 wherein said indicia means are also visually perceptible.

3. The apparatus of claim 1 wherein said body includes anchor means for embedding said body within the tissue.

4. The apparatus of claim 3 wherein said anchor means includes a barb located at one end of said body.

5. The apparatus of claim 3 wherein said anchor means includes a hook located at one end of said body.

6. The apparatus of claim 1 wherein one of said indicia means comprises a marker portion extending from said body.

7. The apparatus of claim 1 wherein one of said indicia means comprises a marker groove formed within said body.

8. The apparatus of claim 1 wherein said plurality of indicia means includes at least two markers which are radiographically differentiable.

9. The apparatus of claim 8 wherein one of said markers indicates a single unit axial length, and the other of said markers indicates a multiple unit axial length.

10. The apparatus of claim 1 wherein said predetermined locations are spaced apart by approximately one centimeter.

11. An apparatus for determining the location of lesions within tissue, said apparatus comprising:

an elongated body;

an anchor portion disposed at one end of said body, said anchor portion adapted to embed said body with the tissue; and a plurality of indicia means located at predetermined, periodic locations on said elongated body, said indicia means being visually perceptible and radiopaque, each one of said indicia means being distinctly perceptible and differentiable from any other of said indicia means, said plurality of indicia means being of sufficient number to extend on said body to outside of the tissue, so that the location of lesions radiographically detected may be determined relative to the axis of said body and the distance of the lesions to the skin of the tissue may thereby be determined.

12. The apparatus of claim 11 wherein said anchor portion includes a barb located at one end of said body.

13. The apparatus of claim 11 wherein said anchor portion includes a hook located at one end of said body.

14. The apparatus of claim 11 wherein one of said indicia means comprises a marker portion extending from said body.

15. The apparatus of claim 11 wherein one of said indicia means comprises a marker groove formed within said body.

16. The apparatus of claim 11 wherein said plurality of indicia means includes at least two markers which are radiographically differentiable.

17. The apparatus of claim 16 wherein one of said markers indicates a single unit axial length, and the other of said markers indicates a multiple unit axial length.

18. The apparatus of claim 11 wherein said predetermined locations are spaced apart by approximately one centimeter.

19. The method of determining the location of lesion tissue to be removed during surgery, said method comprising the steps of:

providing an elongated needle having a hollow axial center;

providing a guidewire adapted to traverse the hollow axial center of the needle, the guidewire including a plurality of indicia means disposed along the axial length of the guidewire, each one of said indicia means being distinctly perceptible and differentiable from any other of said indicia means;

inserting the needle into the body adjacent to the lesion tissue;

depositing the guidewire into the body through the needle;

taking a radiogram when the guidewire is within the body; and determining the axial position of the lesion tissue relative to the indicia means on the guidewire.

20. A method of determining the location of lesion tissue to be removed during surgery, said method comprising the steps of:

providing an elongated needle having a plurality of indicia means disposed along the axial length of the needle, each one of said indicia means being distinctly perceptible and differentiable from any other of said indicia means;

inserting the needle into the body adjacent to the lesion tissue;

taking a radiogram when the needle is within the body; and determining the axial position of the lesion tissue relative to the indicia means on the needle.

* * * * *